United States Patent [19]

Groshong

[11] Patent Number: 5,074,871
[45] Date of Patent: Dec. 24, 1991

[54] CATHETER ATHEROTOME

[75] Inventor: LeRoy E. Groshong, Vancouver, Wash.

[73] Assignee: EVI Corporation, Portland, Oreg.

[21] Appl. No.: 447,888

[22] Filed: Dec. 7, 1989

[51] Int. Cl.$^5$ .................................... A61B 17/32
[52] U.S. Cl. .................................. 606/170; 606/198; 604/22; 604/107
[58] Field of Search ............... 606/159, 170, 167, 180, 606/198; 128/751, 752; 15/104.19; 604/22, 104, 105, 106, 107, 108, 109

[56] References Cited

U.S. PATENT DOCUMENTS

| | | | |
|---|---|---|---|
| 2,655,154 | 10/1953 | Richter | 606/159 |
| 2,730,101 | 1/1956 | Hoffman | 606/180 |
| 2,816,552 | 12/1957 | Hoffman | 606/180 |
| 3,320,952 | 5/1967 | Wright | 128/200.23 |
| 3,435,826 | 4/1969 | Fogarty | 606/200 |
| 3,472,230 | 10/1969 | Fogarty | 606/127 |
| 3,540,431 | 11/1970 | Mobin-Uddin | 128/1 |
| 3,704,711 | 12/1972 | Park | 604/284 |
| 4,020,847 | 5/1977 | Clark, III | 606/180 |
| 4,030,503 | 6/1977 | Clark, III | 128/304 |
| 4,273,128 | 6/1981 | Lary | 606/167 |
| 4,445,509 | 5/1984 | Auth | 606/180 |
| 4,559,927 | 12/1985 | Chin | 606/159 |
| 4,589,412 | 5/1986 | Kensey | 606/180 |
| 4,611,594 | 9/1986 | Grayhack et al. | 606/127 |
| 4,612,931 | 9/1986 | Dormia | 606/127 |
| 4,625,726 | 12/1986 | Duthoy | 606/127 |
| 4,631,052 | 12/1986 | Kensey | 606/159 |
| 4,648,402 | 3/1987 | Santos | 606/198 |
| 4,650,466 | 3/1987 | Luther | 606/198 |
| 4,655,217 | 4/1987 | Reed | 606/159 |
| 4,681,106 | 7/1987 | Kensey et al. | 606/180 |
| 4,706,671 | 11/1987 | Weinrib | 128/348.1 |
| 4,723,549 | 2/1988 | Wholey et al. | 128/344 |
| 4,739,760 | 4/1988 | Chin et al. | 606/171 |
| 4,745,919 | 5/1988 | Bundy et al. | 128/305 |
| 4,755,175 | 7/1988 | Nilsson | 604/268 |
| 4,765,332 | 8/1988 | Fischell et al. | 606/159 |
| 4,768,508 | 9/1988 | Chin et al. | 606/170 |
| 4,790,812 | 12/1988 | Hawkins, Jr. et al. | 604/43 |
| 4,807,626 | 2/1989 | McGirr | 604/107 |
| 4,832,055 | 5/1989 | Palestrant | 128/899 |
| 4,867,156 | 9/1989 | Stack et al. | 606/159 |
| 4,886,061 | 12/1989 | Fischell et al. | 604/22 |
| 4,890,611 | 1/1990 | Monfort et al. | 606/159 |
| 4,895,560 | 1/1990 | Papantonakos | 606/159 |
| 4,966,604 | 10/1990 | Reiss | 606/159 |

Primary Examiner—C. Fred Rosenbaum
Assistant Examiner—William W. Lewis
Attorney, Agent, or Firm—Chernoff, Vilhauer, McClung & Stenzel

[57] ABSTRACT

A catheter atherotome and method for its use for performing partial atherectomy in an artery and thereby enlarging the lumen effectively available for blood flow through the artery. An expansible cutter head at the distal end of a catheter includes several elongate flexible members mounted in a parallel array and spaced angularly apart from one another about the associated ends of two concentric members of the catheter in such a way that longitudinal and rotary relative movement of the members of the catheter selectively either bows the flexible members arcuately outwardly into a cutting position or draws them into alignment parallel with the catheter. A sharpened edge of a blade carried on at least one flexible member extends circumferentially and is directed toward the catheter's proximal end when the flexible members are bowed. Partial removal of an atheroma is effected by manually pulling the cutter head past an atheroma with the sharpened edge exposed, with the speed, force, and amount of expansion of the cutter head determined by the operator. Removal of cut-away pieces of atherosclerotic plaque material is accomplished either by pull-back of a balloon-tipped catheter or by use of a membrane enshrouding the cutter head to trap the shavings.

19 Claims, 3 Drawing Sheets

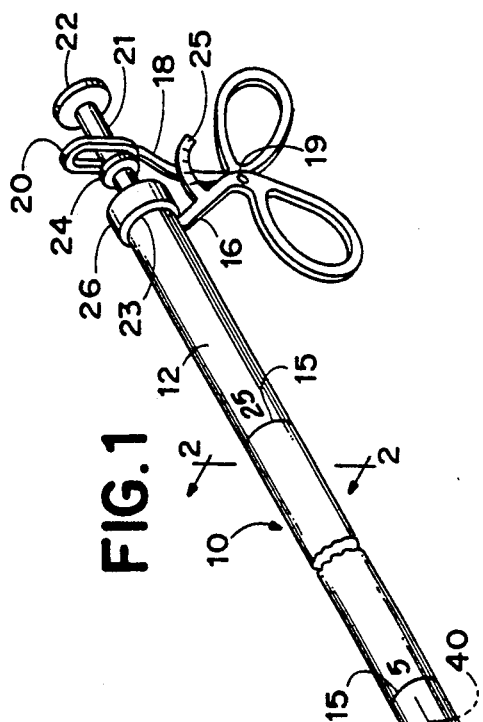
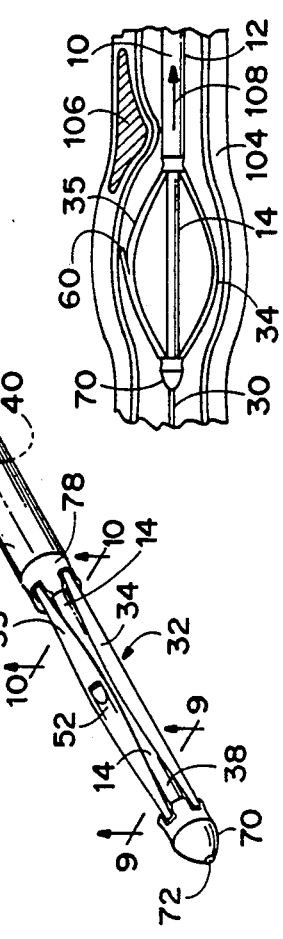
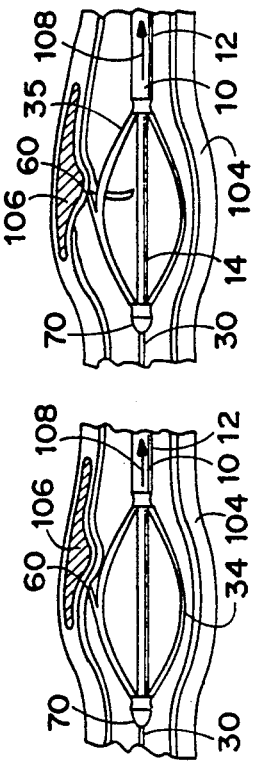
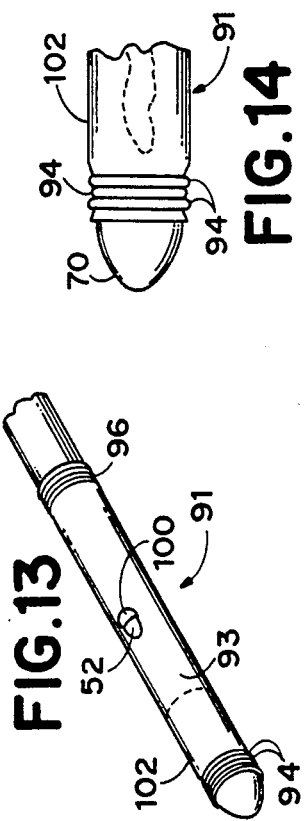
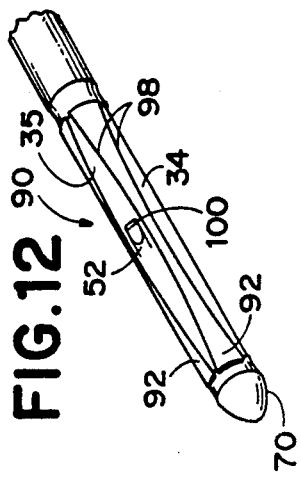

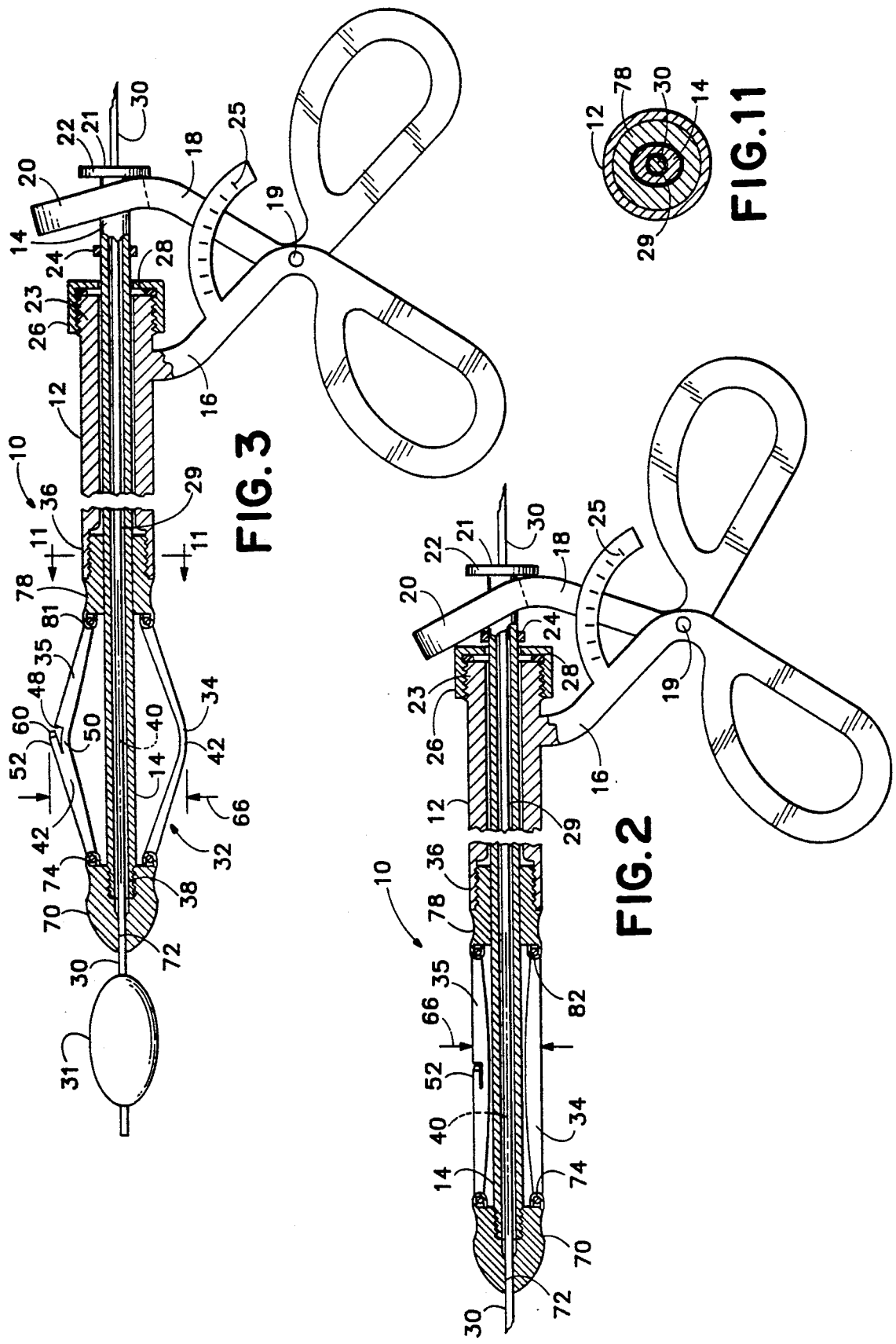

CATHETER ATHEROTOME

BACKGROUND OF THE INVENTION

The present invention relates to surgical apparatus and procedures, and particularly to a device for excising portions of the atherosclerotic plaque material causing stenosis in an artery.

Atherosclerosis is a condition which progressively affects many arteries of the body with advancing age. It ultimately produces thickening of the medial layer of the arterial wall, which may involve some or all of the circumference of the blood vessel. Eventually, significantly narrowed internal diameter, or stenosis, of the artery results and restricts the flow of blood to the tissue beyond the stenosis, producing symptoms including angina or myocardial infarction in the heart, claudication or gangrene in the legs, high blood pressure, or deterioration of kidney function.

The art and science involved in modern vascular surgery are comparatively young and began with the successful end-to-end repair of severed arteries in Korean war casualties. Atherosclerotic narrowing of arteries then could only be corrected by complete endarterectomy, which required a longitudinal incision through the entire narrowed segment of an artery. Exposure of an artery for this purpose was difficult, and the wounds resulting from the surgery were large. Although results were often gratifying, the practice was not widespread because of resulting problems such as pseudoaneurysms developing in endarterized segments and the potential for vessel wall dissection at the distal endpoint, and because of the difficulty posed both for the patient and for the surgeon. During the 1950's a variety of synthetic tubular grafts were introduced and perfected for partial arterial replacement and bypasses around stenoses. Because of the relative ease of such procedures by comparison with endarterectomy, bypass grafting soon became the dominant means of correcting arterial narrowing within the pelvis and thigh. Advances in surgical technique in the late 1960's made possible the use of the patient's own reversed saphenous vein to bypass occluded arteries on the heart and below the knee.

As the population of the United States has aged as a group, the manifestations of atherosclerosis have, as a group, become this nation's number one health problem in terms of both suffering and cost. While surgical bypass procedures using saphenous vein or prosthetic conduit remain the procedure of choice in most instances, newer technologies have evolved in the last decade to simplify the treatment of atherosclerotic stenoses in an attempt to reduce patient risk, reduce cost, and to make treatment available to more people. In carefully selected cases involving narrowing of short segments of the coronary, renal, iliac, and femoral arteries balloon dilation has been employed with some success. Generally, however, the duration of arterial patency resulting from such procedures is less than for bypass graft procedures. Utilization of lasers to open narrowed arteries has not yet proven to be clinically successful and is very expensive in all aspects.

In recent years a variety of atherectomy devices have been used experimentally in attempts to extend patency. Some of these devices include rotary cutting mechanisms, which restrict their use to stenoses of short length. Some are driven by high-speed electric motors which add to their complexity and increase the likelihood of breakdown while also reducing the amount of responsiveness and taking the ability to control operation out of the surgeon's hands.

Manually-operated devices for relieving arterial stenoses are disclosed, for example, in Lary U.S. Pat. No. 4,273,128, which discloses a device having a plurality of curved knife blades whose edges are directed radially outward, and Fischell et al. U.S. Pat. No. 4,765,332, which discloses a catheter including a proximally-exposed annular cutting edge which is no greater in diameter than an outer sleeve of the catheter to which it is attached. Luther U.S. Pat. No. 4,650,466, discloses a catheter which includes an expansible woven tube portion which can be used to abrade atherosclerotic plaque from the interior wall of the artery. Clark, III, U.S. Pat. No. 4,020,847, discloses a catheter device including a slot having sharp edges extending longitudinally of the catheter to free dangling matter attached inside an artery, which might otherwise obstruct the lumen of the artery.

Hoffman U.S. Pat. Nos. 2,730,101 and 2,816,552 disclose teat bistoury devices including blades which can be bowed outwardly along the length of each blade to protrude radially. The device is intended to be rotated to cut away restrictions in a milk canal of a cow's teat.

Several prior art devices useful for manually opening venous valves are disclosed in Chin et al. U.S. Pat. Nos. 4,739,760 and 4,768,508 and Reed U.S. Pat. No. 4,655,217. Chin U.S. Pat. No. 4,559,927 discloses an endarterectomy apparatus including a center-pull annular cutter for removing arteriosclerotic material.

Rotary, mechanically operated devices are disclosed in such patents as Sokolik U.S. Pat. No. 3,320,957, which discloses a device including an array of helical stationary blades inside which an oppositely-twisted helical rotor operates to shear material protruding inwardly between the stationary blades. Auth U.S. Pat. No. 4,445,509 discloses a fluted rotary burr. Kensey U.S. Pat. Nos. 4,589,412 and 4,631,052 disclose turbine-driven rotary devices for opening obstructed arteries, and Kensey et al. U.S. Pat. No. 4,681,106 discloses another turbine-driven rotary cutting device.

Several devices for use in retrieving stones from within bodily passageways by entrapping the stones within baskets including arrays of helical wires are disclosed in Grayhack et al. U.S. Pat. No. 4,611,594, Duthoy U.S. Pat. No. 4,625,726, Dormia U.S. Pat. Nos. 4,347,846 and 4,612,931. Related devices are disclosed by McGirr U.S. Pat. No. 4,807,626, and Hawkins, Jr. et al. U.S. Pat. No. 4,790,812, which discloses a parachute-like basket carried on a distal end of a rotatable interior member of a catheter so that the parachute-like basket can retrieve particles cut free by the interior member of the catheter. Park U.S. Pat. No. 3,704,711 discloses a device in which a radially outwardly disposed edge can be controllably concealed within a distal end of a catheter or exposed so that the blade can be used.

Balloon-tipped catheters are disclosed in Fogarty U.S. Pat. No. 3,435,826, while Fogarty U.S. Pat. No. 3,472,230 discloses a catheter including an umbrella-like skirt useful for retrieval of stones.

There still remains a need, however, for an improved atherectomy device which is simple in concept and operation, manually operable, and immediately responsive, and which is useful for all stenoses regardless of the length of the area of stenosis. There is also a particular need for such a device which can be made small enough for surgical removal of plaque from smaller arteries such as those of the heart.

SUMMARY OF THE INVENTION

The present invention overcomes some of the shortcomings and disadvantages of the devices disclosed in the prior art by providing a catheter atherotome which is manually operable and by which a surgeon can carve away atherosclerotic plaque from within an artery by entering the artery with a catheter at a point proximal to the plaque deposit. The plaque is cut away piece by piece, using serial pullback strokes of an expansible and contractible cutter head carried on the distal end of the catheter. The cutter head is collapsible to a constricted configuration providing a small diameter conforming to the diameter of the catheter itself, or expansible to an appropriate size as determined by the size of an artery where it is to be used. The cutter head of the catheter atherotome of the present invention includes at least one blade carrier and at least one support member, all of which are elongate and flexible. The blade carrier and support member or members are aligned generally parallel with each other when the cutter head is in the collapsed configuration, and are arranged about an inner member of the catheter. The inner member extends distally beyond the distal end of an outer sheath portion of the catheter when the cutter head is in the constricted configuration. Respective ends of each blade carrier and each support member are attached to the inner member and to the outer sheath of the catheter, so that when the distal end of the inner member is moved closer to the distal end of the outer sheath the blade carriers and support members are forced to bow outward, in respective radial planes with respect to the inner member, expanding the cutter head radially to an expanded configuration. When a blade carrier is bowed outward, a sharpened edge of a blade is exposed, directed proximally along the catheter, so that moving the catheter proximally while it is in the expanded configuration brings the sharpened edge to bear against an atherosclerotic plaque deposit to cut it away from the interior of an artery. At least a significant portion of the sharpened edge extends transversely with respect to the length of the catheter, and the inner member and outer sheath of the catheter are prevented from rotating relative to each other, to preserve this orientation of the sharpened edge.

While it is particularly well-adapted for use in the femoral and popliteal arteries, the catheter atherotome of the invention in an appropriate size is also intended for use in the tibial and peroneal arteries and, in smaller size, for use in the heart and renal arteries.

In a preferred embodiment of the invention, the longitudinal position of the inner member of the catheter is adjustable relative to the outer sheath, and the blade carrier and support members are flexible, so that the amount of radial bowing of the elongate members and the degree of exposure of the sharpened edge are controllable. Preferably, the angle of attack of the sharpened edge is adjusted such that it will engage atherosclerotic plaque but not normal arterial lining tissue.

In a preferred embodiment of the invention a single blade carrier and two support members provide a cutting edge over only a minor portion circumference of the cutter head. As a result, atherectomy can be controllably performed on angular sector of the arterial wall in locations such as the femoral artery, where atherosclerosis normally involves only the posterior one half of the artery.

In a preferred embodiment of the invention a flexible membranous sheath is provided to surround the cutter head assembly except where a cutting edge is provided, so that the shavings of plaque are trapped within the cutter head during each cutting pass of the blade over the plaque. This embodiment is intended for use particularly in smaller arteries where it would be awkward or impractical to insert a balloon-tipped catheter beyond a stenosis, or where the catheter atherotome is introduced into an artery percutaneously.

It is, therefore an important object of the present invention to provide an improved catheter atherotome for use in relief of stenoses in arteries.

It is another important object of the present invention to provide such a device which is manually adjustable between a constricted configuration in which a cutting edge is concealed and an expanded configuration in which the cutting edge is operatively positioned and exposed to a degree controllable by the user of the device.

It is an important feature of the apparatus of one embodiment of the present invention that it includes a blade carrier which is flexible, allowing the blade to move between a position in which it moves along the interior of healthy portions of an artery, and a position in which it cuts away atherosclerotic plaque as the cutter head is drawn through a stenosis.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

FIG. 1 is a pictorial view of a catheter atherotome which embodies the present invention, with the catheter portion shown foreshortened, and with the cutter head in a constricted configuration.

FIG. 2 is a sectional view of the catheter atherotome shown in FIG. 1, taken along the line 2—2 of FIG. 1.

FIG. 3 is a view similar to FIG. 2, with the cutter head in an expanded, or cutting configuration.

FIG. 11 is a sectional view of the catheter atherotome shown in FIG. 3, taken along line 11—11, thereof.

FIG. 12 is a pictorial view of the cutter head portion of a catheter atherotome according to the invention, including a plaque-holding membranous sheath portion associated with the blades of the cutter head.

FIG. 13 is a perspective view of a cutter head having a tubular plaque-holding membrane covering the outside of the elongate flexible members.

FIG. 14 is a fragmentary side elevation view showing a detail of the cutter head shown in FIG. 13.

FIGS. 15, 16, and 17 are sectional views of a portion of an artery including a stenosis, showing the action of the cutter head of the catheter atherotome of the present invention as it is drawn past the stenosis to remove a portion of the plaque material forming the stenosis.

DETAILED DESCRIPTION OF THE INVENTION

Figure 4:
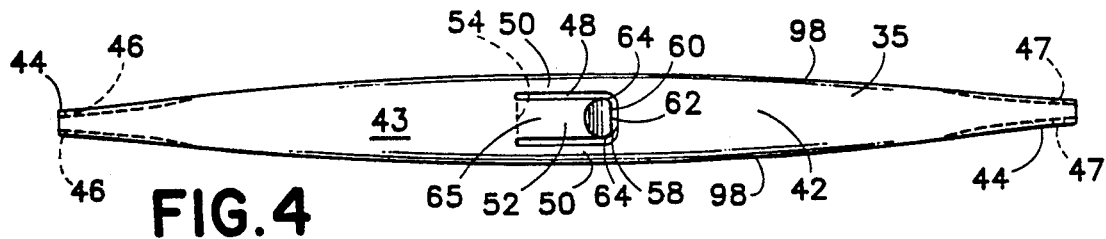
FIG. 4 is a view of the outside of a blade carrier of the cutter head of the atherotome shown in FIGS. 1-3.
Figure 5:
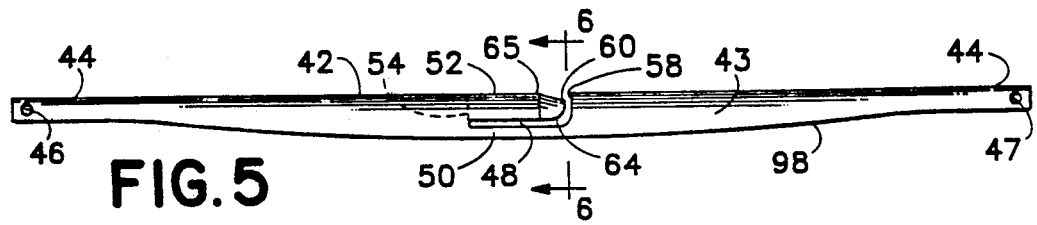
FIG. 5 is a side view of the blade carrier shown in FIG. 4.
Figure 7:
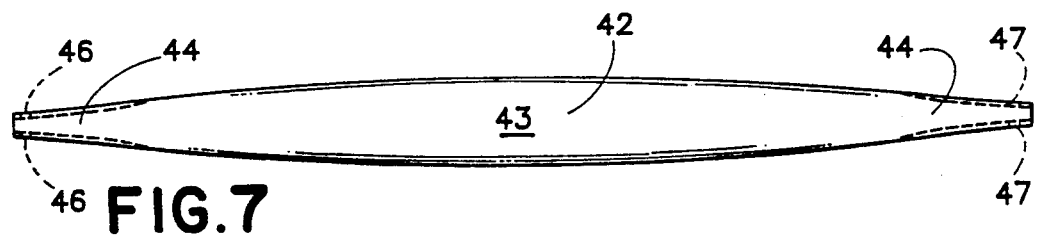
FIG. 7 is a view of the outside of an elongate flexible support member of the cutter head of the atherotome shown in FIGS. 1-3.
Figure 8:
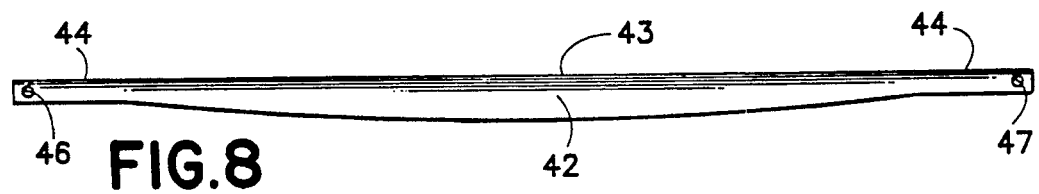
FIG. 8 is a side view of the flexible support member shown in FIG. 7.
Figure 6:
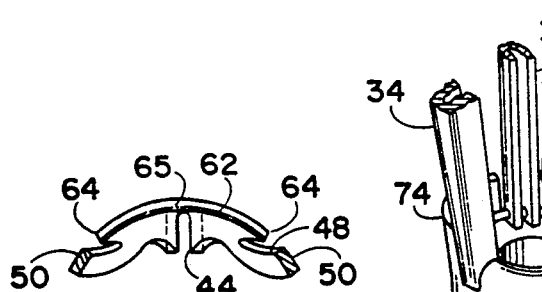
FIG. 6 is a sectional view, at an enlarged scale, of the blade carrier shown in FIG. 5, taken along line 6—6.

Referring now to the drawings which form a part of the disclosure herein, in FIGS. 1-3 a catheter atherotome 10 includes an elongate flexible tubular outer sheath 12. A similar inner member 14 of somewhat greater length is disposed slidably within the of the outer sheath 12. The outer sheath 12 and inner member 14 are flexible enough to negotiate curves in arteries atraumatically, but are rigid enough to maintain relative position between the two, both longitudinally and rotationally. They might be made, for example, of a suitable polyvinyl chloride plastic material, or, possibly of a graphite-fiber-reinforced synthetic plastic resin. Markings 15 may be provided along the outer sheath 12 to indicate the length of the catheter atherotome distal of each marking as an aid to placement in an artery.

A first lever 16 is connected with the outer sheath 12 near its proximal end. A second lever 18 is pivotally connected with the first lever 16 at a pivot joint 19. An elongate loop 20 is attached to the second lever 18 and surrounds the rear or proximal end portion 21 of the inner member 14. A stop 22 is fixedly attached to the proximal end of the inner member 14. Finger loops are provided on the levers 16 and 18 for use in manipulation of the first and second levers 16 and 18 to position the proximal end 21 of the inner member 14 relative to the proximal end 23 of the outer sheath 12, as desired. A second stop 24 is preferably also located on the inner member 14, on the distal side of the loop 20, to be used, if necessary, to push the inner member 14 distally into the proximal end 23 of the outer sheath 12. Preferably, a scale 25 is provided on the first lever 16 as an indicator of the position to which the inner member 14 has been withdrawn relative to the outer sheath 12. A cap 26 is mounted on the proximal, or rear end of the outer sheath 12, preferably by means of mating threads, and an O-ring 28, held in place by the cap 26, grips the exterior surface of the inner member 14 with an appropriately adjustable amount of force to maintain the desired position of the inner member 14 relative to the outer sheath 12.

The inner member 14 is tubular, with a lumen 29 which is large enough to admit passage of a guide wire (not shown) or a balloon-tipped catheter 30 which may, for example, be a Fogarty ® arterial embolectomy catheter. However, the lumen may be too small to admit a balloon-tipped catheter or may be omitted entirely, in an embodiment of the catheter atherotome 10 intended for use in smaller arteries, such as coronary arteries.

A controllably expansible cutter head 32 includes a plurality of elongate flexible members 34 and 35 extending between the distal end 36 of the outer sheath 12 and the distal end 38 of the inner member 14, which extends, as previously mentioned, beyond the distal end 36 of the outer sheath 12. While three elongate flexible members 34 and 35, equiangularly spaced about the inner member 14, are shown and preferred, fewer or more might also be utilized. In the embodiment shown, one of the elongate flexible members is a blade carrier 35, while the remainder are support members 34. The location of the blade carrier 35 with respect to the circumference of the outer sheath 12 and inner member 14 is established as bearing a known relationship to, for example, the attachment of the first lever 16. It would also be possible to have a larger number of blade carriers 35 and a consequently greater angular extent of cutting with each stroke of the atherotome, as will be more fully understood upon consideration of the complete disclosure herein.

The catheter atherotome 10 can be of an appropriate size, depending on the size of the artery in which it is to be used, and larger elongate flexible members 34 and 35 are required for use in larger arteries.

As shown in FIGS. 1 and 2, when the inner member 14 is located with its distal end 38 in a position of maximum extension beyond the distal end 36 of the outer sheath 12, the elongate flexible members 34 and the blade carrier 35 extend closely alongside the protruding portion of the inner member 14, in a generally cylindrical constricted configuration of the cutter head 32, centered about a central longitudinal axis 40.

The elongate flexible support members 34 and the blade carrier 35 are of flexible resilient material such as spring steel sheet material having a midlength portion 42 and a pair of opposite ends 44. The ends 44 are bent into a convex "U" shape and define bores 46 and 47 which pass through the portions forming the legs of the "U" shape at each of the ends 44, as shown in FIGS. 4, 5, 6, 7 and 8. The midlength portion 42 is wider and is also curved, but with a convex outer surface 43 having a greater radius of curvature, as may be seen in FIG. 6, in order to be able to bend more easily than the end portions.

The blade carrier 35 is similar to the support members 34, except that it includes a U-shaped cut defining a blade opening 48 centrally located in the midlength portion 42, leaving a pair of laterally separated, longitudinally extending, lateral portions 50, one on each side of the blade opening 48.

A blade 52, which may be a continuation of the material of the midlength portion 42 of the blade carrier 35, extends from a distally located first end 54 of the blade opening toward a proximal end 58 of the blade opening 48 and resembles generally the shape of a human fingernail. The proximal end 58 of the blade opening is closer to the end portion 44 of the blade carrier 35 which is attached to the distal end 36 of the outer sheath. The blade 52 has a sharpened edge 60 which extends generally transversely relative to the length of the blade carrier 35 and faces toward the proximal end 58 of the blade opening 48. The sharpened edge 60 preferably includes a central portion 62 which is arcuately curved as seen in a plane perpendicular to the central longitudinal axis 40 of the cutter head 32 (see FIG. 6), but relatively straight as seen looking radially inward toward the cutter head 32 (see FIG. 4). Lateral portions 64 of the sharpened edge 60 are arcuately curved toward the sides of the blade 52, so that when in a cutting position, the blade can excise a strip of plaque from the interior wall of an artery, cutting free the sides of such a strip without tearing the tissue. The sides of the blade, parallel with the lateral portions 50, however, are not sharpened.

Preferably, the sharpened edge 60 is prepared by grinding the outer surface 65 of the blade 52 to taper toward the radially inner surface of the blade. As a result, the sharpened edge 60 is located a small distance radially inward from the extension of the outer surface 43 at the proximal end 58 of the blade opening 48 when the cutter head 32 is in the constricted configuration as shown in FIGS. 1 and 2. Thus, the sharpened edge 60 will not unintentionally cut the interior surface of an artery as the catheter atherotome 10 is being withdrawn.

The catheter 30 extending through the catheter atherotome 10 has a balloon tip 31 which extends beyond the distal end of the catheter atherotome 10, as may be seen in FIG. 1. The catheter 30 is longer than the entire catheter atherotome 10, so that it can be manipulated at the proximal end of the catheter atherotome 10 while extending through the lumen 29 defined within the inner member 14, as shown in FIGS. 2 and 3. Such length is also desirable to provide room for cutting strokes of the atherotome with the balloon tipped catheter 30 located stationary in an artery.

The midlength portions 42 of each elongate flexible member 34, 35 are flexible in response to movement of the inner member 14 relative to the outer sheath 12, so that retraction of the distal end 38 of the inner member with respect to the distal end 36 of the outer sheath results in flexure of the elongate flexible blade carrier 35 and the associated support members 34 of the cutter head 32 to achieve the expanded configuration shown in FIG. 3. The support members 34 and the blade carrier 35 extend to define generally respective radial planes radiating from the central longitudinal axis 40. It will be understood that other forms of construction of the support members 34 and blade carriers 35 besides those described herein are also possible, with the objective being to provide blade carriers and support members which are flexible to provide outward bow-like bending in radial planes. The diameter 66 of the cutter head in its expanded configuration is determined by both the length of each elongate flexible member 34 or 35 and the degree to which the inner member 14 is withdrawn proximally within the distal end 36 of the outer sheath 12.

When the cutter head 32 is adjusted to its expanded configuration the blade carrier 35 bends primarily in the lateral portions 50. The blade 52, attached at the distal end 54 of the blade opening, extends in the direction established by the adjacent material of the blade carrier 35, so that the sharpened edge 60 is exposed in a location radially outside the lateral portions 50.

Figures 9, 10:
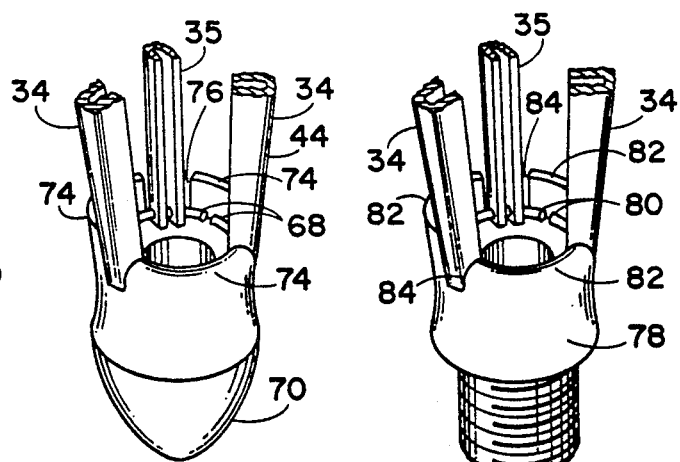
FIG. 9 is a perspective view, taken in the direction indicated generally by line 9—9 of FIG. 1, showing a fitting for attaching the distal end of each elongate flexible member to the end of the inner member of the catheter atherotome shown in FIGS. 1-3.
FIG. 10 is a perspective view, taken in the direction indicated generally by the line 10—10 in FIG. 1, of the fitting attaching the proximal ends of the elongate flexible members to the distal end of the outer sheath portion of the catheter atherotome shown in FIGS. 1-3.

As may be seen with reference more particularly to FIGS. 9 and 10, as well as to FIGS. 2 and 3, the elongate flexible support members 34 and the blade carrier 35 are prevented from rotating with respect to the inner member 14 and outer sheath 12 by the manner in which they are attached. An articulating mounting ring 68 extends through the bores 46 of all of the several elongate flexible members 34 and 35. The articulating mounting ring 68 is securely attached to a cutter head distal fitting 70, which has an ogival shape. The cutter head distal fitting 70 is attached to the distal end 38 of the inner member 14 by exterior threads defined on the inner member 14 and interior threads in the distal fitting 70. A bore 72 in the distal fitting 70 is an extension of the lumen 29 of the inner member 14.

The articulating mounting ring 68 is attached to the proximal end of the cutter head distal fitting 70 by a plurality of tethering hasps 74 disposed about the proximal end of the distal fitting 70 and equal in number to the number of elongate flexible members 34 and 35 to be attached to the distal fitting 70. Each of the tethering hasps 74 is bent inwardly to form an arch over the articulating mounting ring 68, although some are shown in an unbent condition in FIG. 9. Adjacent ones of the several tethering hasps 74 cooperatively define radially extending slots 76 between one another, with the distal end 44 of a respective one of the elongate flexible members 34 and 35 being disposed within each of the slots 76. The slots 76, bores 46, and articulating mounting rings 68 prevent each of the elongate flexible members 34 and 35 from rotating about an axis parallel with the central longitudinal axis 40, but permit the distal end portion 44 of each elongate flexible member 34, 35 to pivot about the articulating mounting ring 68 as the elongate flexible members 34 and 35 are bowed in respective radial planes with respect to the central longitudinal axis 40.

A proximal cutter head fitting 78 is attached to the distal end 36 of the outer sheath 12 by exterior threads on the fitting 78 mated with interior threads defined in the outer sheath 12. An articulating mounting ring 80, similar to the articulating mounting ring 68, extends through the several bores 47 defined by the proximal end portions 44 of the elongate flexible members 34, 35, interconnecting the proximal ends of all of the elongate flexible members 34, 35 with the proximal fitting 78. The articulating mounting ring 80 is attached to the cutter head proximal fitting 78 by a plurality of tethering hasps 82 equal in number to the total number of elongate flexible members 34 and 35.

Similar to the tethering hasps 74, the tethering hasps 82 extend from the distal face of the cutter head proximal fitting 78 and are bent arcuately inward toward the central longitudinal axis 40 of the catheter atherotome 10, although for clarity some of the hasps are shown unbent in FIG. 10. The hasps 82 are arched over the articulating mounting ring to retain it and the attached proximal end portions 44 of the elongate flexible blade carrier 35 and support members 34. The tethering hasps 82 define radially extending slots 84 between adjacent ones of the hasps 82 and prevent the proximal end portions 44 of the several elongate flexible members 34 and 35 from rotating about an axis parallel with the central longitudinal axis 40 of the catheter atherotome 10. The proximal end portions 44 of the blade carrier 35 and support members 34 are free to pivot about the articulating mounting ring 80 to the expanded position shown, for example, in FIG. 3 in response to retraction of the distal end 38 of the inner member 14 into the distal end 36 of the outer sheath 12.

In order to establish the location and preserve the transverse orientation of the sharpened edge 60, and particularly the central portion 62, the inner member 14 is prevented from rotating within the outer sheath 12 by providing mating non-circular surfaces. For example, as shown in FIG. 11 the inner member 14 may have an ovoid cross-section shape, and the proximal fitting 78 may have a corresponding interior surface shape, permitting longitudinal, but not rotational relative movement.

The blade 52 preferably is stiff enough so that the angle of incidence of the sharpened edge 60 is stable, once the amount of flexure of the blade carrier 35 is established. The blade 52 can thus pare off a thin slice of atherosclerotic plaque or similar material from the interior of an artery during use of the catheter atherotome 10 equipped with the cutter head 32 of the invention.

The cutter head 32 provides cutting edge coverage over only a small angular sector of the interior circumference of an artery. The support members 34, being without sharpened edges, slip along the interior surface of the artery and keep the cutter head 32 centered within the arterial lumen.

In some instances, as in coronary arteries, a catheter atherotome may be required to be of a size that is too small to admit passage of the balloon-tipped catheter 30 therethrough. It is still absolutely imperative to retrieve pieces of plaque as they are cut free from the interior wall of an artery. In order to recover the matter excised from an arterial wall, a cutter head 90, shown in FIG. 12, which is otherwise similar to the cutter head 32, additionally includes a flexible membrane in the form of a sheath 92 arranged about and attached to the elongate flexible members 34 and 35. One end of the membranous sheath 92 is attached to the cutter head distal fitting 70 by means of ferrules 94 and the other end is attached to the cutter head proximal fitting 78 by means of ferrules 96. The sheath 92 is preferably adherently attached to the elongate flexible support members 34 and blade carrier 35, at least along their longitudinal margins 98, and a slit 100 or an equivalent opening is provided to expose the sharpened edge 60 and provide ingress for pieces of plaque into the space within the cutter head. Pieces of plaque or the like cut free from the interior wall of an artery are able to pass through the slit 100 in the same manner in which wood shavings pass along the blade of a plane, into the interior of the cutter head 90, to be collected upon retrieval of the catheter atherotome from within an artery.

As shown in FIG. 13, in a cutter head 91 a membranous sheath 93 which is tabular may be used to surround the blade carrier 35 and support members 34 (not shown) which are similar to the corresponding parts of the cutter head 32. The sheath 93 may be attached in the same manner as is the sheath 92.

The membrane material used as the sheath 92 or 93 must be flexible and thin, yet strong and elastic enough to accommodate the adjustment of the cutter head 90 or 91 to its expanded configuration. One suitable material is a thin sheet latex. The membranous sheath 92 or 93 may be attached to distal fitting 70 and the proximal fitting 78 after assembly of the cutter head 90 or 91.

A distal portion 102 of the sheath 92 or 93 may be of a suitably porous material acting as a filter. For example, an expanded polytetrafluoroethylene (PTFE) membrane may be supported on suitable woven material, in order to allow unclotted whole blood to pass through the porous material, while the particles of plaque excised by the cutter head 91 are retained inside the sheath 93, as shown in FIG. 14.

Referring now to FIGS. 15, 16 and 17, showing a portion of an artery 104 including an atheroma 106, the cutter head 32 of the catheter atherotome 10 is illustrated schematically to show its use. As shown in FIG. 15, the catheter atherotome 10 has been inserted into the artery from right to left while the cutter head 32 is in the constricted configuration. Thereafter, the inner member 14 has been withdrawn a distance into the distal end 36 of the outer sheath 12, so that the elongate flexible members 34 and 35 are bowed. This places the midlength portion 42 of each support member 34 at an increased radial distance away from the inner member 14 and similarly causes the blade carrier 35 to carry the blade 52 to a greater radial distance from the inner member 14, and places placing the sharpened edge 60 in an exposed position.

To excise a portion of the atheroma 106, the catheter atherotome is manually pulled to the right as indicated by the arrow 108 in FIG. 16. As the inwardly projecting atheroma 98 is encountered by the blade 52, and particularly by the sharpened edge 60, the sharpened edge 60 begins to cut a portion of the plaque material free, in the form of a thin strip. The convex shape of the outer surface 64 of the blade 52 helps to control the angle of incidence of the sharpened edge 60, to prevent it from digging too deeply and thus cutting through an arterial wall. Where there is no plaque material present, the sharpened edge 60 of the blade 52 is exposed radially outwardly of the outer surface 43 of the blade carrier 35 adjacent the proximal end of the blade opening, but is oriented so that it does not catch the intima of the arterial wall and simply slides along the interior wall of the artery without doing any cutting.

The surgeon using the catheter atherotome 10 can repeatedly move the cutter head 32 back and forth lengthwise of an artery in the area of an atheroma such as the atheroma 108, cutting away a thin, narrow strip of plaque with each movement of the cutter head 32 in the direction indicated by the arrow 100 in FIGS. 12b and 12c, until the lumen of the artery 96 has been opened sufficiently. While it should not usually be necessary, the cutter head 32 can be placed in the constricted configuration during distal movement following a cutting stroke. After each cutting stroke the entire catheter atherotome 10 should be rotated within the artery through an angle about the central axis 40 which can be determined by the position of the levers 16 and 18, so as to result in excision of plaque in an evenly distributed pattern about the interior of the artery. Thereafter, the inner member 14 is returned to its position extended further beyond the distal end 36 of the outer sheath 12, using the loop 20 (see FIG. 1) to push as necessary against the second stop 24, thus retracting the midlength portions 42 of the elongate flexible members 34 and 35 closer to the inner member 14, and returning the cutter head 32 to its constricted configuration. The catheter atherotome 10 can then be withdrawn from the artery, followed by withdrawal of the balloon-tipped catheter 30, with the balloon 60 (see FIG. 1) remaining inflated to retrieve the material which has been cut free from the arterial wall during the process.

Figure 18:
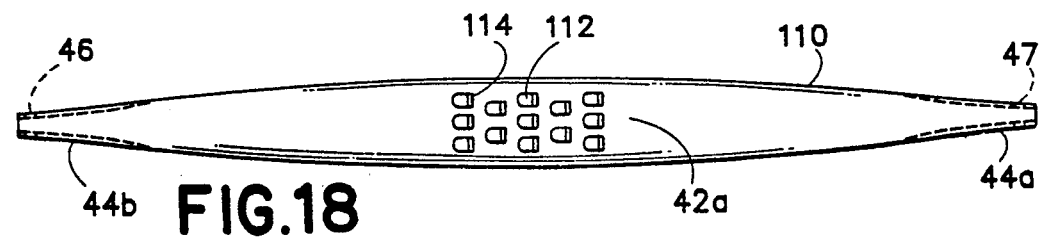
FIG. 18 is a view of an alternative form of blade carrier useful in a catheter atherotome according to the invention.

An alternative blade carrier 110, useable in place of a blade carrier 35 and shown in FIG. 18, is of an elongate flexible design basically similar to that of the blade carrier 35. It includes a proximal end portion a, a midlength portion 42a, and a distal end portion b. The end portions are U-shaped, as are the end portions 44 of the blade carrier 35 and support members 34, and define respective bores 46 and 47. The blade carrier 110 has several small blades 112 similar to those of some cheese graters, each blade 112 having an outwardly protruding arcuate sharpened edge 114 facing toward a proximal end portion 44a. An outwardly protruding arcuate throat portion supports each blade 112, and provides a respective opening between the sharpened edge and the adjacent portion of the blade carrier 110. Material cut free by the blades 112 will be directed inwardly through the respective opening into the interior of the cutter head 32 equipped with the blade carrier 110, in the same way as pieces of cheese are directed into a cheese grater.

The catheter atherotome 10 may be introduced into an artery including a stenosis by providing access to the artery and opening the arterial wall at a position more proximal to the heart than the location of the stenosis. Preferably, a guide wire is introduced into the artery and directed past the stenosis. Thereafter, if required, a dilator, such as a dilating balloon catheter, may be introduced into the artery, guided by the wire, and used to dilate the stenosis to a diameter at which it can accept the catheter atherotome 10. The dilator may then be withdrawn and the catheter atherotome 10 according to the present invention may be inserted into the artery along the guide wire to a position just beyond the stenosis. The guide wire may then be withdrawn and replaced by the balloon-tipped catheter 30. After inflation of the balloon 31 to prevent loss of pieces of material cut free from the arterial wall by the atherotome 10, the cutter head 32 may be expanded to the required size by squeezing together the finger loops of the levers 16 and 18, withdrawing the inner member 14 into the distal end 35 of the outer member 12 a required distance. The elongate loop 20 acts upon the stop 22 to withdraw the proximal end 21 of the inner member 14 at the proximal end of the catheter atherotome 10. Preferably, the scale 25 provided on the lever arm 16 may be used to determine when the inner member 14 has been withdrawn sufficiently to provide the required expansion of the cutter head 32.

Thereupon, the cutter head 32 may be withdrawn past the location of the atheroma, with the sharpened edge 60 of the blade 52 paring away a portion of the plaque from the interior of the artery. The atherotome 10 is then pushed into the artery until the blade 52 is again beyond the atheroma, and is rotated about the central axis 40 to a desired position for a subsequent pull-back cutting stroke, using the levers 16 and 18 as indicators of the amount of rotation of the atherotome 10 within the artery. After several strokes, for example, six to ten cutting strokes, sufficient enlargement of the lumen of the artery should have taken place, and the cutter head 32 can be returned to its constricted configuration, contracting the flexible support members 34 and blade carrier 35 into position alongside the inner member 14 as shown in FIG. 1, so that the catheter atherotome 10 can be positioned from the artery with the sharpened edge 60 safely positioned so that it will not harm the lining of the artery.

The procedure is similar when using the catheter atherotome having a cutter head 90 or 91 (FIG. 12), except that the material cut free from the arterial wall would be retained within the membranous sheath 92 for retrieval along with the cutter head 90 or 91 when it is withdrawn from the artery.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A catheter atherotome for use in surgical removal of plaque from the interior wall of an artery, comprising:
   (a) an elongate tubular outer sheath having respective proximal and distal ends;
   (b) an elongate inner member disposed within said outer sheath and having respective proximal and distal ends, said distal end of said inner member extending beyond said distal end of said outer sheath;
   (c) a cutter head including a plurality of elongate flexible members each having a proximal end interconnected with said outer sheath and a distal end interconnected with said inner member;
   (d) means for moving said inner member longitudinally with respect to said outer sheath so as to flex said elongate flexible members from a constricted configuration of said cutter head into an expanded configuration of said cutter head; and
   (e) at least one of said elongate flexible members being a blade carrier having a blade carried thereon, said blade defining a respective sharpened edge, at least a portion of said sharpened edge extending generally transversely with respect to the length of said blade carrier and facing generally toward said proximal ends of said outer sheath and said inner member.

2. The catheter atherotome of claim 1 wherein at least one of said elongate flexible members is a support member free from sharpened edges.

3. The catheter atherotome of claim 1 wherein said cutter head has a generally cylindrical form when in said constricted configuration.

4. The catheter atherotome of claim 1 wherein said elongate flexible members extend generally parallel with and arranged at regular spacing about said elongate inner member when said cutter head is in said constricted configuration.

5. The catheter atherotome of claim 1 wherein said sharpened edge is located radially outward beyond said blade carrier when said cutter head is in said expanded configuration.

6. The catheter atherotome of claim 1, including means associated with said elongate inner member and said outer sheath for preventing rotation of said inner member relative to said outer sheath.

7. The catheter atherotome of claim 1 wherein said blade carrier is of resiliently flexible material and includes a pair of laterally apart-spaced lateral portions extending longitudinally, said blade carrier defining a blade opening therebetween, said blade carrier also defining respective first and second ends of said blade opening, and said blade being attached to said blade carrier proximate said first end of said blade opening and extending between said lateral portions toward said second end of said blade opening.

8. The catheter atherotome of claim 7, said blade having an outer surface which is convexly arcuate, and said sharpened edge being arcuate and including a pair of oppositely located lateral portions and a central portion, said lateral portions of said sharpened edge being located radially closer to said inner member than is said central portion of said sharpened edge.

9. The catheter atherotome of claim 8, said central portion of said sharpened edge being farther than said lateral portions from said first end of said blade opening.

10. The catheter atherotome of claim 7, said blade carrier having a convex outer surface and said sharpened edge of said blade being in a position located radially inwardly from said outer surface of said blade carrier and proximate said second end of said blade opening when said cutter head is in said constricted configuration.

11. The catheter atherotome of claim 10 wherein said blade has an outer surface which is outwardly convex, so as to resemble a human fingernail, said sharpened edge corresponding to the edge of a human fingernail.

12. The catheter atherotome of claim 1, said flexible elongate members of said cutter head defining respective spaces therebetween and said cutter head including flexible membrane means associated therewith, for enclosing said spaces between said flexible elongate members while preserving said blade opening in said blade carrier, and for collecting within said cutter head material which has been excised from said interior wall of an artery.

13. The catheter atherotome of claim 12 wherein at least a portion of said flexible membrane means is pervious to unclotted whole blood, but impervious to pieces of plaque excised from said interior wall by said blade.

14. The catheter atherotome of claim 12 wherein said flexible membrane means includes means for retaining said material which has been excised from said interior wall of said artery while permitting escape of unclotted whole blood from within said cutter head.

15. A method of performing partial atherectomy of an artery to enlarge the effective lumen thereof, comprising:

(a) making an opening through a wall of an artery at a location spaced apart from an atheroma and more proximal to a patient's heart than said atheroma;

(b) inserting a catheter atherotome, having an expansible cutter head including a plurality of elongate flexible members, at least one of which is a blade carrier carrying a blade including a sharpened edge extending substantially transversely, into said artery through said opening;

(c) directing said catheter atherotome along the interior of said artery to the vicinity of said atheroma with said cutter head in a constricted configuration in which said sharpened edge is prevented by said blade carrier from cuttingly engaging the interior of said artery;

(d) directing and moving said catheter atherotome further along the interior of said artery until said cutter head passes beyond said atheroma;

(e) expanding said cutter head controllably and flexing said blade carrier, thereby exposing said sharpened edge to face in a proximal direction, so that said sharpened edge is located radially outward from a portion of said blade carrier which prevented said sharpened edge from cuttingly engaging the interior of said artery prior to the step of expanding said cutter head; and (f) thereafter manually retracting said catheter atherotome along said artery a distance great enough to being said sharpened edge into cutting engagement with said atheroma and disrupt the surface of said atheroma by longitudinal retrogression of said catheter atherotome and said blade of said cutter head.

16. The method of claim 15 including, after said step of manually retracting said catheter atherotome, the further step of returning said catheter atherotome cutter head to said constricted configuration and again moving said catheter atherotome along the interior of said artery until said cutter head again passes beyond said atheroma; thereupon again expanding said cutter head within said artery; and thereafter again retracting said catheter atherotome along said artery a distance great enough to being said sharpened edge into cutting engagement with said atheroma to cut away a portion of said atheroma by longitudinal retrogression of said cutter head.

17. The method of claim 15 including the subsequent steps of redirecting and moving said catheter atherotome along the interior of said artery until said cutter head passes again beyond said atheroma; rotating said catheter atherotome through an angle about a central axis thereof to direct said blade toward a different angular sector of the circumference of said artery; and thereafter manually retracting said catheter atherotome along said artery a distance great enough to being said sharpened edge into cutting engagement with said atheroma and to cut away a portion of said atheroma by longitudinal retrogression of said catheter atherotome and said blade of said cutter head.

18. The method of claim 15 including cutting away a thin, narrow strip of plaque from a portion of said atheroma when retracting said catheter atherotome with said sharpened edge in cutting engagement with said atheroma.

19. The method of claim 15 including the step of orientating said cutter head by rotating said catheter atherotome through an angle about a central axis thereof to direct said blade toward a predetermined angular sector of said artery.

* * * * *